(12) United States Patent
Sasaki et al.

(10) Patent No.: US 6,210,704 B1
(45) Date of Patent: Apr. 3, 2001

(54) MEDICAL ADHESIVE DRESSING AND FIRST-AID ADHESIVE TAPE

(75) Inventors: Yasuyuki Sasaki; Masayoshi Kuniya; Takashi Kinoshita; Takahiro Kousaka; Osamu Ohira, all of Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 09/479,600

(22) Filed: Jan. 7, 2000

(30) Foreign Application Priority Data

Jan. 14, 1999 (JP) .................................................. 11-007175
Jan. 14, 1999 (JP) .................................................. 11-007176
Jan. 14, 1999 (JP) .................................................. 11-007177
Jan. 14, 1999 (JP) .................................................. 11-007178

(51) Int. Cl.$^7$ ............................. A61F 13/00; A61F 13/02
(52) U.S. Cl. ........................................... 424/443; 424/448
(58) Field of Search ............................. 604/704; 424/448, 424/449, 423

(56) References Cited

U.S. PATENT DOCUMENTS

| 3,870,593 | * | 3/1975 | Elton et al. ........................... 161/159 |
| 4,166,464 | | 9/1979 | Korpman . |
| 5,503,076 | | 4/1996 | Yeo . |
| 5,648,167 | | 7/1997 | Peck . |
| 5,713,842 | | 2/1998 | Kay . |
| 5,795,834 | * | 8/1998 | Deeb et al. ............................ 442/62 |
| 5,914,282 | * | 6/1999 | Dunshee et al. ....................... 442/76 |

FOREIGN PATENT DOCUMENTS

| 0 371 808A2 | 6/1990 | (EP) . |
| 0 651 984 A2 | 5/1995 | (EP) . |
| WO 91/13638 | 9/1991 | (WO) . |
| WO 96/28113 | 9/1996 | (WO) . |
| WO 99/37336 | 7/1999 | (WO) . |

OTHER PUBLICATIONS

Japanese Industrial Standard, Surface Roughness Definition and Designation, Standardization Journal, Tokyo, Japan, pp. 1–19, 1994.*

Annex to the International Search Report.

European Search Report.

* cited by examiner

*Primary Examiner*—Thurman K. Page
*Assistant Examiner*—Isis Ghali
(74) *Attorney, Agent, or Firm*—Sughrue, Mion, Zinn, Macpeak & Seas, PLLC

(57) ABSTRACT

A medical adhesive dressing comprising a polyolefin-based backing film having a medical pressure-sensitive adhesive layer on one surface thereof and a print layer on the other surface thereof, the adhesive dressing having surface properties that cause no wrinkle upon winding and unwinding thereof. For example, the surface of the polyolefin-based film preferably has a surface roughness (10-point average roughness) of 2 to 12 $\mu$m on the side where a print layer is to be formed. The olefin-based film is preferably an ethylene-vinyl acetate copolymer film or a three-layer film comprising an ethylene-methyl methacrylate copolymer layer/A-B-A type block copolymer layer/ethylene methyl methacrylate copolymer layer. It is used for application to skin as a first-aid adhesive tape, large-size adhesive tape, dressing, or draping used in the field of medical and hygiene fields. It can provide medical adhesive dressing and first-aid adhesive tape whose surface causes no printing failure.

20 Claims, No Drawings

MEDICAL ADHESIVE DRESSING AND FIRST-AID ADHESIVE TAPE

BACKGROUND OF THE INVENTION

1. Field of the Invention

The present invention relates to a medical adhesive dressing used for applying to the skin in the field of medical therapy and hygiene. More particularly, the present invention relates to a medical adhesive dressing used advantageously in a first-aid adhesive tape or a large size adhesive tape, a dressing material, a drape material, etc. The present invention also relates to a first-aid adhesive tape having such a medical adhesive dressing.

2. Description of the Related Art

Medical adhesive dressings usually include a backing film having an adhesive layer on one surface thereof and upon use it is applied to a desired skin surface through the adhesive layer.

The backing films for use in an adhesive dressing for use in medical applications are mostly those which comprise flexible polyvinyl chloride as a main component in view of their skin following property (flexibility) while they are applied to the skin, stretchability (contraction and expansion properties), feeling, etc.

Generally, flexible polyvinyl chloride contains a plasticizer in a large amount in order to impart it with flexibility. It has been pointed out some problems. That is, the plasticizer migrates into the adhesive layer of the adhesive dressing so that its cohesion decreases and the phenomenon of adhesive residue or a decrease in adhesion power occurs. Recently, from the viewpoint of placing importance to environment, movement is being developed in various fields for trying as much as possible to reduce the amount of polyvinyl chloride resins, which contain chlorine, a species of halogen harmful to environment.

Accordingly, polyolefin resins are being given attention as a substitute for polyvinyl chloride resin and study has been made on the usability as the backing film for adhesive dressings for medical use. The backing film made of polyolefin resin is excellent in flexibility and stretchability and is useful as a polyvinyl chloride substituted film.

In the commercialization of such a medical adhesive dressing, it is usually the case that first-aid adhesive tapes or large-size adhesive tapes are manufactured as having a print layer on one surface of the backing film thereof. That is, usually first-aid adhesive tapes and large-size adhesive tapes are devised such that one surface of the backing film is printed by pattern printing in a color resembling human skin. For example, they are provided with patterns of grids, semi-continuous or continuous crosses, etc. so that the adhesive dressing does not attract attention. Products may also be manufactured with multi-color printing.

SUMMARY OF THE INVENTION

However, it has hitherto been difficult to form such a print layer or cutting of film tends to occur when winding or a polyolefin film after the printing in the form of a roll or unwinding it, particularly when the film is thin.

For example, generally, in the case of pattern printing, the film before forming a pressure-sensitive adhesive layer thereon is printed and then a pressure-sensitive adhesive layer is formed. Upon forming a print layer, the backing film needs to be unwound (let out) and if the surface is too smooth, the letting out property is aggravated due to the adhesion between the film surfaces, which sometimes results in the breakage of the film as the case may be. Entrapment of air (bubble) when winding up the film increases the possibility of the occurrence of creases in the backing film. Printing on such creases could cause printing failure, such as lack of print, etc. If the surface a backing film is too smooth, it will be abraded when medical adhesive dressings or first-aid adhesive tapes containing it are in use as applied to the skin. As stated above, in the case of medical adhesive dressings comprising a polyolefin film with a pattern print layer on one surface thereof, it is important to adjust the surface roughness of the film.

When a single-color pattern is applied on a surface of the backing film, generally printing is carried out at a relatively high speed so that minute creases, if any, would result in lack of print. Therefore, the adjustment of the surface roughness of the printing surface is very important.

In case where a multi-color print is applied on a surface of the film, colors are applied one after another in precise registration. Therefore, minute creases if present upon winding the film tends to cause lack of print. In this regard, the adjustment of surface roughness of the printing surface is very important.

As a result of their intensive research, the present inventors have found that the surface conditions of at least one of a polyolefin film as a backing film of an adhesive dressing and a printing layer formed thereon influence winding workability and further printability of the resulting film. They have found that these properties can be improved by adjustment of the surface roughness of the backing film. In other words, the present inventors have found that there is an optimal region for the surface roughness of a film surface.

More specifically, they have found that adjustment of the surface roughness of the surface of the backing film on the side the printing layer to a level within a predetermined range provides a medical adhesive dressing that is excellent in film winding workability and printing layer forming property. Further, they have found that this reduces the abrasion of the printing layer while the adhesive dressing is used. Also, they have found that such adjustment results in excellent workability, gives high quality feeling, and improves slidability upon rubbing against clothes or dresses during the medical adhesive dressing is applied and used.

Therefore, in one aspect, the present invention provides a medical adhesive dressing comprising a polyolefin-based backing film having a medical pressure-sensitive adhesive layer on one surface thereof and a print layer on the other surface thereof, said adhesive dressing having surface properties that cause no wrinkle upon winding and unwinding thereof.

The surface properties of said adhesive dressing may be obtained by adjustment of at least one of property of a surface of the backing film on a side where a print layer is to be formed and property of a surface of the backing film on a side where a pressure-sensitive adhesive layer is to be formed.

The surface of the backing film on the side where a print layer is to be formed preferably has a surface roughness (10-point average roughness) of 2 to 12 $\mu$m.

The surface of the backing film on the side where a pressure-sensitive adhesive layer is to be formed preferably has a surface roughness (10-point average roughness) of 2 to 40 $\mu$m.

Preferably, the surface roughnesses on the both surfaces of the polyolefin-based backing film differ one from the other.

Preferably the surface roughnesses on the both surfaces of the polyolefin-based backing film differ one from the other.

The surface roughness of the surface of the backing film on the side where a pressure-sensitive adhesive layer is to be formed is preferably greater than the surface roughness of the surface of the backing film on the side where a print layer is to be formed.

The polyolefin-based backing film may be one of an ethylene-vinyl acetate copolymer film and a three-layer film comprising an ethylene-methyl methacrylate copolymer layer/A-B-A type block copolymer layer/ethylene methyl methacrylate copolymer layer.

The ethylene-vinyl acetate copolymer may have a vinyl acetate content of 15 to 28% by weight.

The ethylene-vinyl acetate copolymer may have a weight average molecular weight of $1 \times 10^4$ to $1 \times 10^5$, a molecular weight distribution of 4 or less, and a melt flow rate of 3 g/10 minutes or less.

The A-B-A type block copolymer may be one of a styrene-butadiene-styrene block copolymer and a styrene-isoprene-styrene block copolymer.

The ethylene-methyl methacrylate copolymer layer may be a layer that contains an ethylene-methyl methacrylate copolymer and low density polyethylene.

The ethylene-methyl methacrylate copolymer layer may comprise a micro domain structure comprising an ethylene-methyl methacrylate copolymer as a continuous phase and low density polyethylene as a discontinuous phase.

The print layer may comprise ultraviolet-curing type ink.

The polyolefin-based backing film may be white in color due to inclusion of a white filler.

The pressure-sensitive adhesive layer may have a separator applied to one surface thereof.

In another aspect, the present invention provides a first-aid adhesive tape comprising a medical adhesive dressing as described above and an absorbent pad in a central region of the medical adhesive dressing.

The above and other objects, effects, features and advantages of the present invention will become more apparent from the following description of preferred embodiments.

DETAILED DESCRIPTION OF THE INVENTION

In the present invention, the polyolefin film that can be used for the medical adhesive dressing includes not only polymers of hydrocarbon based unsaturated monomers, typically polyethylene and ethylene-propylene copolymers but also copolymers of the hydrocarbon based unsaturated monomers with modifier monomers. Specifically, preferred examples of the polymer constituting the polyolefin film include polyethylene, polypropylene, ethylene-propylene copolymers, ethylene-butene-1 copolymers, ethylene-octene-1 copolymers, ethylene-methyl methacrylate copolymers, ethylene-methacrylic acid copolymers, ethylene-vinyl acetate copolymers, polypropylene-polybutene mixtures, polyethylene-polybutene mixtures. At least one selected from these polyolefin-based resins can be used advantageously.

Also, the olefin-based film used in the present invention is not only a single-layer film but also a multilayer film. In the case of a multilayer film, it is sufficient for at least one of the unit layers of multilayer is a polyolefin-based film. For example, the multilayer film may be of the following construction: polyolefin-based film/modifier resin film, polyolefin-based film/modifier resin film/polyolefin-based film, modifier resin film/polyolefin-based film/modifier resin film, etc. Such a modifier includes, for example, A-B-A type block copolymers, such as styrene/butadiene/styrene tri-block copolymers and styrene/isoprene/styrene tri-block copolymers.

Among the above polyolefin films, those films that can be used advantageously in respect of flexibility and stretchability, appropriate tensile strength and the like include ethylene-vinyl acetate copolymer films, or a three-layer film of a construction: ethylene-methyl methacrylate copolymer layer/A-B-A type block copolymer layer/ethylene-methyl methacrylate copolymer layer. Of the above films, those in which the A-B-A type block copolymer is a styrene-butadiene-styrene block copolymer or a styrene-isoprene-styrene block copolymer are more preferable.

In the case where the polyolefin-based film used is an ethylene-vinyl acetate copolymer film, it is preferred to use ethylene-vinyl acetate copolymers that have vinyl acetate contents in the range of 15 to 28% by weight, preferably 20 to 25% by weight, in view of appropriate elasticity, flexibility, and stretchability. Also, it is preferred to use ethylene-vinyl acetate copolymers that have weight average molecular weights in the range of $1 \times 10^4$ to $1 \times 10^5$ and relatively narrow molecular weight distributions as low as 4 or less, preferably 3.5 or less. Further, it is preferred to use ethylene-vinyl acetate copolymers having low flowabilities, i.e., having melt-flow rates measured according to JIS K-6730 of 3 g/10 minutes or less in order to impart appropriate tensile strength to the resulting film when they are molded into a film.

The ethylene-methyl methacrylate copolymer layer that constitutes the above three-layer films is preferably a layer that contains an ethylene-methyl methacrylate copolymer and a low-density polyethylene. When the film contain a low-density polyethylene, the polyethylene is not compatible with the resin of the film and remains in the film in a finely dispersed state, so that appropriate unevenness is generated in the surface of the film by the fine particles of the low-density polyethylene. As a result, the resulting film can be imparted high quality feeling and at the same time the adhesion (anchoring effect) to a printing layer to be formed on the surface of the film can be improved. In this case, the amount of low-density polyethylene to be blended in the ethylene-methyl methacrylate copolymer layer is usually about 5 to about 45% by weight, preferably 15 to 35% by weight, based on the total weight of the ethylene-methyl methacrylate copolymer layer.

When the film contains a low-density polyethylene as described above, the resin components may be compatible with each other and mixed to form a homogeneous entity. However, it is preferred that the resin components form a so-called micro-domain structure (sea-island structure) rather than the resin components are compatible with each other and are made homogeneous. In this micro-domain structure, the ethylene-methyl methacrylate copolymer constitutes the matrix (sea) and the low-density polyethylene is dispersed as a discontinuous phase (islands) in the matrix.

If the resin components are rendered homogeneous, it is only possible to obtain films having intermediate properties, or average properties, of the properties that the respective resin components have. On the contrary, the above micro-domain structure allows the properties of the respective resin components to be separately exhibited to some extent, so that adjustment of compounding amounts of respective resin components enables to one to obtain desired properties.

The polyolefin films obtained as described above are molded to have a thickness of about 10 to about 200 µm, preferably 30 to 130 µm, before it can be used for the medical adhesive dressing of the present invention. A surface of the film on which a pressure-sensitive adhesive layer is formed is preferably subjected to a treatment for improving the anchoring effect upon formation of the pressure-layer sensitive adhesive layer, such as a corona discharge treatment or coating of a known primer.

In the production of the medical adhesive dressing of the present invention, a pressure-sensitive adhesive layer is formed on one surface of the above polyolefin. The pressure-sensitive adhesive is not particularly limited and may be any one that is used as a pressure-sensitive adhesive for medical use. Preferred examples of the pressure-sensitive adhesive include acrylic-based pressure-sensitive adhesives, rubber-based pressure-sensitive adhesives, silicone-based pressure-sensitive adhesives, and blends of two or more of them.

The acrylic-based pressure-sensitive adhesive which can be used are preferably homopolymers of (meth)acrylic acid esters having an alkyl group containing 1 to 18 carbon atoms, preferably 4 to 12 carbon atom, and copolymers that comprise such an ester as a main component monomer and one or more copolymerizable monomers (for example, functional monomer(s), etc.) in amounts in the range of 3 to 50% by weight, preferably 5 to 40% by weight.

Examples of the above (meth)acrylic acid alkyl esters include esters, such as butyl ester, hexyl ester, octyl ester, decyl ester, lauryl ester, and stearyl ester. The ester chain may be linear or branched.

The monomers copolymerizable with the above esters include functional monomers, or example, (meth)acrylic hydroxyalkyl esters such as (meth)acrylic acid 2-hydroxyethyl ester and (meth)acrylic aid 3-hydroxypropyl ester, carboxyl group-containing unsaturated monomers such as (meth) acrylic acid, maleic acid, fumaric acid and crotonic acid, (meth)acrylamide and derivatives thereof, such as (meth)acrylamide, dimethyl (meth)acrylamide and diethyl (meth)acrylamide, N-alkoxyalkyl (meth)acrylamide such as N-butoxymethyl (meth)acrylamide, N-butoxymethyl (meth)acrylamide, and N-ethoxymethyl (meth)acrylamide, (meth)acrylic acid N,N-alkylaminoalkyl esters such as (meth) acrylic acid N,N-dimethylaminoethyl ester, acid amide group-containing unsaturated monomers such as N-vinylpyrrolidone, etc. In addition to the functional monomers, there may be copolymerized non-functional monomers such as vinyl acetate, styrene, α-methylstyrene, and (meth)acrylonitrile.

Examples of the rubber-based pressure-sensitive adhesive that can be used in the pressure-sensitive adhesive layer may be a blend of a main material resin (such as natural rubber, polyisobutylene, polyisoprene, polybutene, a styrene-isoprene (or butadiene) -based block copolymer, or an ethylene-vinyl acetate copolymer) and a tackifier as a side material (such as rosin-based resin, terpene-based resin, chroman-indene resin, terpene-phenol-based resin, or petroleum-based resin). Softening agents such as liquid polybutene, mineral oils, lanolin, and liquid polyisoprene, fillers such as titanium oxide and clay, antioxidants such as butyl hydroxytoluene, etc. Such a side material may be blended with the acrylic-based pressure-sensitive adhesive.

Further, the silicone-based pressure-sensitive adhesive used as the pressure-sensitive adhesive includes, for example, a pressure-sensitive adhesive that comprises polydimethylsiloxane as a main ingredient.

The pressure-sensitive adhesive having the above-described composition is formed on the backing film to a thickness of about 10 to about 200 $\mu$m, preferably 20 to 100 $\mu$m to provide the medical adhesive dressing of the present invention.

In the medical adhesive dressing of the present invention, the polyolefin-based film used as a backing film is formed on one surface thereof (opposite to the surface where the pressure-sensitive adhesive layer is formed) with a single color pattern print layer or a multi-color print layer.

In the case where a single color print layer is to be formed, the print layer may be formed with ink of any desired color by known printing means. From the viewpoint of productivity and economy, it is preferred that the print layer be formed by gravure printing. The color of printing ink is preferably one resembling the color of skin of humans so that the medical adhesive dressing or their processed products such as first-aid adhesive tapes when applied to the skin surface are inconspicuous. The print pattern may be of continuous or discontinuous repetition of the same pattern, such as grids, for example, cross pattern, elliptic, circular, or the like pattern.

On the other hand, in the case of multi-color print layer, the print layer may be formed by multi-step printing using a plurality of colors, such as cyan, magenta, yellow, black, gold, and silver. It is preferred that ultraviolet curing type ink. Forming a print layer with ultraviolet curing type ink will increase printing speed and printing precision. This is effective particularly for character printing.

In the present invention, upon forming characters or the like images on a surface of a polyolefin-based film by single color printing or multi-color printing, it is preferred to add various fillers such as titanium white, zeolite, and zinc white to the film. This is to render the film whiter so that sharpness of prints or hiding power can be increased.

In one embodiment, the medical adhesive dressing and first-aid adhesive tape of the present invention is adjusted with respect to the surface roughness of the polyolefin-based film used as a backing film to a specified range. That is, the surface roughness of the backing film on the side where the print layer is formed is adjusted within the range such that wrinkle will not occur when the adhesive dressing is wound or unwound, for example, within the range of a surface roughness (10-point average roughness) of 2 to 12 $\mu$m, preferably 3 to 8 $\mu$m. The surface roughness as used herein means 10-point average as measured according to the method prescribed in JIS B0601.

The above construction ensures an escape for the air entrained between the films when the polyolefin-based film is wound into a roll. As a result, no wrinkle occurs in the film, so that the occurrence of printing failure (non-printing) in a later step due to wrinkle can be prevented.

In addition, when the polyolefin film in a roll form is unwound and a medical pressure-sensitive adhesive layer is formed on one surface of the film, the film slides well upon unwinding. In particular, cutting of the polyolefin-based film will not occur even when it is thin and no wrinkle will be generated when the film is wound around a take-up roll. If the surface roughness is below 2 $\mu$m, the above effect sometimes is difficult to be exhibited. On the other hand, a surface roughness of above 12 $\mu$m makes it difficult to form a print layer although the above effect can be obtained.

Also, the surface roughness of the polyolefin-based film used in the present invention is adjusted to 2 to 12 $\mu$m on the side where a print layer is to be formed as described above. In this case, it is preferred that the other side (the side where a pressure-sensitive adhesive is to be applied) of the polyolefin-based film be adjusted. In this case, the surface roughness of the film is adjusted within a range of 2 to 40 $\mu$m, more preferably 10 to 30 $\mu$m.

That is, to bond a medical pressure-sensitive adhesive layer on a surface of a polyolefin-based film closely and strongly, i.e., to improve the anchoring effect between the polyolefin-based film and the medical pressure-sensitive adhesive layer, it is preferable that the surface of the film on the side where the medical pressure-sensitive adhesive is to be applied is subjected to corona discharge treatment or priming treatment as described above. However, another approach for increasing the anchoring effect is to increase close contact surface area (adhesion surface area). Accordingly, it is effective to roughen the surface of the polyolefin-based film and an effective surface roughness is 2 μm or more. If the surface roughness is above 40 μm, there is the fear that the printing ink cannot be coated thoroughly or uniformly. To balance these factors, a surface roughness of 2 to 40 μm is acceptable.

Also, in the present invention, to satisfy both printability and workability during the production process, it is preferred that the surface roughnesses on the both surfaces of the polyolefin-based film differ from each other. More preferably, the surface of the film on the side where a medical pressure-sensitive adhesive layer is has a surface roughness greater than that of the surface on the side where a print layer is formed. This is to secure the anchoring of the film with the medical pressure-sensitive adhesive layer.

The medical adhesive dressing and first-aid adhesive tape of the present invention can be produced by the following method, for example.

First method (with a multi-color printing layer)

First, a polyolefin-based film is molded to a predetermined thickness by a calendar extrusion method or inflation extrusion method. The both surfaces of the resulting polyolefin-based film are roughened by a known means such as an emboss roll, if desired, so that the surface roughness of the film can be adjusted to a predetermined range, e.g., in the range of 2 to 12 μm.

Next, on the side of the polyolefin-based film where a medical pressure-sensitive adhesive layer is to be formed, a pressure-sensitive adhesive solution for forming a medical pressure-sensitive adhesive layer is applied by a direct transfer method in which the adhesive solution is coated directly on the film and dried. Alternatively, the medical pressure-sensitive adhesive solution may be applied to the film by coating the adhesive on a separator having subjected to a separation treatment and dried to form a medical pressure-sensitive adhesive layer of a predetermined thickness and the resulting pressure-sensitive adhesive layered is transferred to the surface of polyolefin-based film.

In this case, to increase the anchoring between the pressure-sensitive adhesive layer and the polyolefin-based film, it is preferred that the surface of the polyolefin-based film on the side where a pressure-sensitive adhesive layer is to be formed is subjected to corona discharge treatment or priming treatment.

Next, on one surface of the polyolefin-based film, is coated ultraviolet-curing ink. In this case, the film is subjected to corona discharge treatment for increasing the adhesion of ink, if desired. Then, the ink is dried and cured. Thus, there is obtained a medical adhesive dressing of the present invention having on one surface thereof a multi-color print layer.

Alternatively, a surface of a polyolefin-based film whose surface roughness has been adjusted to, for example, 2 to 12 μm, is subjected to corona discharge treatment for increasing the adhesion before printing, if desired. Then, on the surface of the film is coated printing ink using ultraviolet-curing ink. The ink is dried and cured to obtain the medical adhesive dressing of the present invention having on one surface thereof a multi-color print layer. Second Method (With a single-color pattern print layer)

First, the polyolefin-based film is molded to a predetermined thickness by calendar extrusion method or inflation extrusion method. The both surfaces of the resulting polyolefin-based film, if desired, is roughened to a specified surface roughness range, for example, in the range of 2 to 12 μm, by a known means such as an emboss roll.

Next, on the polyolefin-based film whose surface roughness ahs been adjusted to, for example, 2 to 12 μm, is coated printing ink, which is dried to form a medical adhesive dressing of the present invention having on one surface thereof a single color pattern print layer. To improve the adhesion of the printing ink, it is preferred that the printing surface be subjected to corona discharge treatment in advance.

Then, on the side of the polyolefin-based film where a medical pressure-sensitive adhesive layer is to be formed, a pressure-sensitive adhesive solution for forming a medical pressure-sensitive adhesive layer is applied by a direct transfer method in which the adhesive solution is coated directly on the film and dried. Alternatively, the medical pressure-sensitive adhesive solution may be applied to the film by coating the adhesive on a separator having subjected to a separation treatment and dried to form a medical pressure-sensitive adhesive layer of a predetermined thickness and the resulting pressure-sensitive adhesive layered is transferred to the surface of polyolefin-based film.

In this case, to increase the anchoring between the pressure-sensitive adhesive layer and the polyolefin-based film, it is preferred that the surface of the polyolefin-based film on the side where a pressure-sensitive adhesive layer is to be formed is subjected to corona discharge treatment or priming treatment.

To produce first-aid adhesive tapes using the medical adhesive dressing, an absorbent pad such as gauze, non-woven fabric, woven fabric, foamed resin or the like is provided in a central region on the surface of the pressure-sensitive adhesive layer of the above-produced medical adhesive dressing (raw fabric). Further one or two separators are laminated thereon and the resulting composite is cut to a predetermined shape. Thus, the first-aid adhesive tape of the present invention can be obtained.

As described above, the medical adhesive dressing and first-aid adhesive tape of the present invention use a polyolefin-based film having a specified surface roughness. Therefore, they can exhibit such properties desired for medical adhesive dressing, such as flexibility and stretchability, satisfactorily enough to serve as substitutes for the conventional medical adhesive dressings that use polyvinyl chloride-based films. The medical adhesive dressing of the present invention has various effects that in particular, upon forming a print layer, no wrinkle occurs and excellent workability is obtained. At the same time, no printing failure results attributable to the occurrence wrinkles. Further the abrasion of print layer when in use is minimized.

EXAMPLES

Hereafter, the present invention will be described more concretely by examples. However, the present invention is not limited thereto and various application or modifications may be made without departing from the technical idea of the present invention.

Example 1

To 100 parts by weight of ethylene-vinyl acetate copolymer having a vinyl acetate content of 25% by weight was added 1 part by weight of a fatty acid-based lubricant and the mixture was molded into a sheet of about 80 g/m² by a calendering method at a temperature of 100 to 140° C.

Then, at a temperature of 70 to 120° C., the resulting sheet was pressed by a roll having a surface roughness of about 5 µm on its surface on the side where a print layer was to be formed. Also, it was pressed by a roll having a surface roughness of about 5 µm on its surface on the side where a pressure-sensitive adhesive layer was to be formed. Thus, a polyolefin-based backing film was prepared.

On the other hand, a monomer mixture consisting of 85 parts by weight of isononyl acrylate, 12 parts by weight of vinyl acetate, and 3 parts by weight of acrylic acid was dissolved in 60 parts by weight of ethyl acetate. To this was added 0.3 part by weight of azobisisobutyronitrile as a polymerization initiator. Polymerization reaction was conducted at 55 to 65° C. for about 10 hours. Thereafter, the reaction mixture was diluted with ethyl acetate to prepare a medical pressure-sensitive adhesive solution having a solids content of 30% by weight.

A separator was separation-treated with a silicone resin on one surface thereof and on the thus-treated surface was coated the above-prepared medical pressure-sensitive adhesive solution to a thickness (dry basis) of 35 µm and dried to form a medical pressure-sensitive adhesive.

Then, one surface of the polyolefin-based film prepared as described above was subjected to corona discharge treatment and a polyolefin backing film as pressed on the surface of the medical pressure-sensitive adhesive such that the treated surface contacted the medical pressure-sensitive adhesive layer to prepare a medical adhesive dressing.

On the surface of the resulting medical adhesive dressing on the side where a print layer was to be formed was applied a character print by multi-color printing. Thereafter, the medical adhesive dressing was processed into a first-aid adhesive tape. Thus, the first-aid adhesive tape of the present invention was prepared.

Example 2

About 80 g/m² three-layer lamination sheet (thickness ratio: 20%/60%/20%) was molded by three-layer simultaneous inflation method at a temperature of 150 to 200° C. so that the following layer arrangement was obtained. That is, a sheet of 100 parts by weight of ethylene-methyl methacrylate having a methyl methacrylate content of 25% by weight was positioned on the side where a print layer was to be formed. Then a sheet of 100 parts by weight of styrene-butadiene-styrene block copolymer having a melt flow rate of 2 g/10 minutes and 1 part by weight of butylhydroxytoluene was placed as an intermediate layer. Finally, a sheet of ethylene-methyl methacrylate copolymer having a methyl methacrylate content of 25% by weight was positioned on the side where a medical pressure-sensitive adhesive layer was to be prepared.

A first-aid adhesive tape was prepared using a medical pressure-sensitive adhesive in the same manner as in Example 1 except that the above-prepared polyolefin-based backing film was used.

Example 3

A three-layer film was prepared in the same manner as in Example 2 except that as the intermediate layer was used a sheet of 100 parts by weight of styrene-isoprene-styrene block copolymer having a melt flow rate of 3 g/10 minutes, 1 part by weight of butylhydroxytoluene and 5 parts by weight of titanium oxide.

A first-aid adhesive tape was prepared using a medical pressure-sensitive adhesive in the same manner as in Example 1 except that the above-prepared polyolefin-based backing film was used.

Example 4

To 100 parts by weight of ethylene-vinyl acetate copolymer having a vinyl acetate content of 25% by weight was added 1 part by weight of a fatty acid-based lubricant and 5 parts by weight of titanium oxide. The mixture was molded into a sheet of about 80 g/m² by a calendering method at a temperature of 100 to 140° C.

Then, at a temperature of 70 to 120° C., the resulting sheet was pressed by a roll having a surface roughness of about 5 µm on its surface on the side where a print layer was to be formed. Also, it was pressed by a roll having a surface roughness of about 20 µm on its surface on the side where a pressure-sensitive adhesive layer was to be formed. Thus, a polyolefin-based backing film was prepared.

A first-aid adhesive tape was prepared using a medical pressure-sensitive adhesive in the same manner as in Example 1 except that the above-prepared polyolefin-based backing film was used.

Example 5

Then, at a temperature of 70 to 120° C., the sheet prepared in Example 4 was pressed by a roll having a surface roughness of about 10 µm on its surface on the side where a print layer was to be formed. Also, it was pressed by a roll having a surface roughness of about 5 µm on its surface on the side where a pressure-sensitive adhesive layer was to be formed. Thus, a polyolefin-based backing film was prepared.

A first-aid adhesive tape was prepared using a medical pressure-sensitive adhesive in the same manner as in Example 4 except that the above-prepared polyolefin-based backing film was used.

Comparative Example 1

A first-aid adhesive tape was prepared in the same manner as in Example 4 except that the both surfaces of the polyolefin-based backing film was pressed by a mirror surface to obtain a very smooth surface (surface roughness of about 1 µm).

Comparative Example 2

A first-aid adhesive tape was prepared in the same manner as in Example 4 using the same medical pressure-sensitive adhesive as in Example 4 except that the polyolefin-based film was prepared by pressing the sheet obtained in Example 4 at a temperature of 70 to 120° C., by a roll having a surface roughness of about 20 µm on its surface on the side where a print layer was to be formed and by a roll having a surface roughness of about 5 µm on its surface on the side where a pressure-sensitive adhesive layer was to be formed.

The first-aid adhesive tapes obtained in the above examples and comparative examples were evaluated as follows. The results are shown in Table 1.

<Winding workability>

Upon preparing the first-aid adhesive tapes of each example and each comparative example, frequencies of occurrence wrinkles by entrapment of air bubble upon winding the polyolefin-based film or medical adhesive dressing raw fabric and upon winding them after corona discharge treatment were examined. Criteria for judgment were as follows.

⊚: No occurrence of wrinkle
○: Occurrence of very slight wrinkles
X: Wrinkles occurred to such an extent that printing failure occurred.

<Surface Roughness>

Under the atmosphere at 23° C., the surface roughness of a polyolefin-based film was measured according to JIS B0601. As the measuring apparatus was used Surf Test 501 manufactured by Mitsutoyo Co., Ltd. and 10-point average roughness was obtained at a standard length of 0.8 mm.

<Printability>

In each of examples and comparative examples, ultraviolet-curing type ink was coated on a surface of each medical adhesive dressing using a commercially available printing apparatus. The ink was cured to apply the surface a 4-color character print. Then, judgment was made if the character could be printed sharply. Criteria for the judgment were as follows.

⊚: Printing was good.
○: Print was slightly dim.
X: Non-sharp print.

TABLE 1

| Evaluation item | | Example | | | | | Comparative Example | |
|---|---|---|---|---|---|---|---|---|
| | | 1 | 2 | 3 | 4 | 5 | 1 | 2 |
| Winding workability | | ○ | ○ | ○ | ⊚ | ○ | X*1 | ⊚ |
| Surface roughness | Print layer side | 4.2 | 3.9 | 3.7 | 4.7 | 10.1 | 1.3 | 21.1 |
| | Pressure-sensitive Layer side | 5.2 | 4.8 | 3.8 | 20.3 | 4.6 | 1.1 | 4.7 |
| Printability | | ⊚ | ⊚ | ⊚ | ⊚ | ○ | ⊚*2 | X |

*1Upon patch tests conducted by applying a first-aid adhesive tape to fingers of the hand, dropping-off occurred. This would be considered to be attributable to abrasion because of deteriorated slipperiness.
*2The portions where wrinkles occurred were impossible to be judged so that judgement was made where no wrinkle was observed.

*1: Upon patch tests conducted by applying a first-aid adhesive tape to fingers of the hand, dropping-off occurred. This would be considered to be attributable to abrasion because of deteriorated slipperiness.

*2: The portions where wrinkles occurred were impossible to be judged so that judgement was made where no wrinkle was observed.

Examples 6 to 10 and Comparative Examples 3 and 4

In Examples 1 to 5 and Comparative Examples 1 and 2, medical adhesive dressings were prepared in the same manner as in Example 1 except as follows. That is, instead of applying multi-color print after a pressure-sensitive adhesive layer was applied, first the surface of the polyolefin-based film on the side where a print layer was to be formed was subjected to corona discharge. Then, a grid pattern skin color print was applied using a gravure coater. This was subjected to corona discharge treatment on the surface where a pressure-sensitive adhesive layer was to be formed. Then, the polyolefin-based backing film was pressed on the surface of the above medical pressure-sensitive adhesive layer such that the treated surface contacted the medical pressure-sensitive adhesive layer. This medical adhesive dressing was used to prepare the first-aid adhesive tape of the present invention.

In the same manner as in Examples 1 to 5 and Comparative 1 and 2, test was conducted and similar results to those in Table 1 were obtained.

The invention may be embodied in other specific forms without departing from the spirit or essential characteristics thereof. Therefore, the present embodiment is to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A medical adhesive dressing comprising a polyolefin-based backing film having a medical pressure-sensitive adhesive layer on one surface thereof and a print layer on the other surface thereof, wherein the surface of said backing film on the side where a print layer is to be formed has a surface roughness of 2 to 12 μm as measured using the 10-point average method of JIS B0601 and the surface of said backing film on the side where a pressure-sensitive adhesive layer is to be formed has a surface roughness 2 to 40 μm as measured using the 10-point average method of JIS B0601.

2. The medical adhesive dressing as claimed in claim 1, wherein the surface roughnesses on the both surfaces of the polyolefin-based backing film differ one from the other.

3. The medical adhesive dressing as claimed in claim 2, wherein the surface roughness of the surface of the backing film on the side where a pressure-sensitive adhesive layer is to be formed is greater than the surface roughness of the surface of the backing film on the side where a print layer is to be formed.

4. The medical adhesive dressing as claimed in claim 1, wherein the polyolefin-based backing film is one of an ethylene-vinyl acetate copolymer film and a three-layer film comprising an ethylene-methyl methacrylate copolymer layer/A-B-A block copolymer layer/ethylene methyl methacrylate copolymer layer.

5. The medical adhesive dressing as claimed in claim 4, wherein the ethylene-vinyl acetate copolymer has a vinyl acetate content of 15 to 28% by weight.

6. The medical adhesive dressing as claimed in claim 4, wherein the ethylene-vinyl acetate copolymer has a weight average molecular weight of $1 \times 10^4$ to $1 \times 10^5$, a molecular weight distribution of 4 or less, and a melt flow rate of 3 g/10 minutes or less.

7. The medical adhesive dressing as claimed in claim 4, wherein the A-B-A block copolymer is one of a styrene-butadiene-styrene block copolymer and a styrene-isoprene-styrene block copolymer.

8. The medical adhesive dressing as claimed in claim 4, wherein the ethylene-methyl methacrylate copolymer layer is a layer that contains an ethylene-methyl methacrylate copolymer and low density polyethylene.

9. The medical adhesive dressing as claimed in claim 8, wherein the ethylene-methyl methacrylate copolymer layer comprises a micro domain structure comprising an ethylene-methyl methacrylate copolymer as a continuous phase and low density polyethylene as a discontinuous phase.

10. The medical adhesive dressing as claimed in claim 1, wherein the print layer comprises ultraviolet-curing ink.

11. The medical adhesive dressing as claimed in claim 1, wherein the polyolefin-based backing film is white in color due to inclusion of a white filler.

12. A first-aid adhesive tape comprising a medical adhesive dressing as claimed in claim 1 and an absorbent pad in a central region of the medical adhesive dressing.

13. The first-aid adhesive tape as claimed in claim 12, further comprising a separator layer on said pressure-sensitive adhesive layer and said absorbent pad.

14. A medical adhesive dressing comprising: a backing film consisting essentially of a molded polyolefin-based polymer film, within which porosity has not been intentionally increased, a medical pressure-sensitive adhesive layer provided on one surface of said backing film, and a print layer on the other surface of said backing film, wherein the surface of said backing film on the side where a print layer is to be formed has a surface roughness of 2 to 12 sum as measured using the 10-point average method of JIS B0601 and the surface of said backing film on the side where a pressure-sensitive adhesive layer is to be formed has a surface roughness of 2 to 40 sum as measured using the 10-point average method of JIS B0601.

15. The medical adhesive dressing as claimed in claim 14 wherein the surface roughness on the both surfaces of the polyolefin-based backing film differ one from the other.

16. The medical adhesive dressing as claimed in claim 14, wherein the surface roughness of the surface of the backing film on the side where a pressure-sensitive adhesive layer is to be formed is greater than the surface roughness of the surface of the backing film on the side where a print layer is to be formed.

17. A first-aid adhesive tape comprising a medical adhesive dressing as claimed in claim 9 and an absorbent pad in a central region of the medical adhesive dressing.

18. The first-aid adhesive tape as claimed in claim 17, further comprising a separator layer on said pressure-sensitive adhesive layer and said absorbent pad.

19. The medical adhesive dressing as claimed in claim 1 wherein the polyolefin-based film is a surface layer film.

20. The medical adhesive dressing as claimed in claim 14 wherein the polyolefin-based backing film is a surface layer film.

* * * * *

UNITED STATES PATENT AND TRADEMARK OFFICE
CERTIFICATE OF CORRECTION

PATENT NO. : 6,210,704 B1
DATED : April 3, 2001
INVENTOR(S) : Yasuyuki Sasaki, Masayoshi Kuniya, Takashi Kinoshita, Takahiro Kousaka, Osamu Ohira It is certified that error appears in the above-identified patent and that said Letters Patent is hereby corrected as shown below:

Column 13, claim 14,
Line 13, delete "sum" and insert -- µm --.
Line 17, delete "sum" and insert -- µm --.

Column 14, claim 17,
Line 8, delete "9" and insert -- 5 --.

Signed and Sealed this

Sixth Day of November, 2001

Attest:

NICHOLAS P. GODICI
Attesting Officer    Acting Director of the United States Patent and Trademark Office